(12) United States Patent
Konno et al.

(10) Patent No.: US 12,182,995 B2
(45) Date of Patent: Dec. 31, 2024

(54) INFORMATION PROCESSING DEVICE, INFORMATION PROCESSING METHOD, AND INFORMATION PROCESSING PROGRAM

(71) Applicant: FUJIFILM CORPORATION, Tokyo (JP)

(72) Inventors: Shinichiro Konno, Kanagawa (JP); Yoshie Fujimoto, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 596 days.

(21) Appl. No.: 17/485,529

(22) Filed: Sep. 27, 2021

(65) Prior Publication Data

US 2022/0101523 A1 Mar. 31, 2022

(30) Foreign Application Priority Data

Sep. 30, 2020 (JP) ................. 2020-166464

(51) Int. Cl.
*G06T 7/00* (2017.01)
(52) U.S. Cl.
CPC .. *G06T 7/0012* (2013.01); *G06T 2207/30068* (2013.01)
(58) Field of Classification Search
CPC ......... G06T 7/0012; G06T 2207/30068; A61B 6/0414; A61B 6/461; A61B 6/502; A61B 6/545
See application file for complete search history.

(56) References Cited

U.S. PATENT DOCUMENTS

2008/0087830 A1 4/2008 Kashiwagi
2009/0299218 A1 12/2009 Holler et al.
(Continued)

FOREIGN PATENT DOCUMENTS

JP 2007-236805 A 9/2007
JP 2008-036279 A 2/2008
(Continued)

OTHER PUBLICATIONS

English language translation of the following: Office action dated Apr. 18, 2023 from the JPO in a Japanese patent application No. 2020-166464 corresponding to the instant patent application. This office action translation is submitted now in order to supplement the understanding of the cited references which are being disclosed in the instant Information Disclosure Statement.
(Continued)

*Primary Examiner* — Chuong A Ngo
(74) *Attorney, Agent, or Firm* — SOLARIS Intellectual Property Group, PLLC

(57) ABSTRACT

An information processing device including at least one processor, wherein the processor is configured to control an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

12 Claims, 13 Drawing Sheets

(56) References Cited

U.S. PATENT DOCUMENTS

2014/0328458 A1    11/2014  Erhard et al.
2017/0172531 A1     6/2017  Sugiyama et al.
2017/0243379 A1*    8/2017  Arai ..................... G16H 50/30
2020/0253572 A1     8/2020  Nakamaya

FOREIGN PATENT DOCUMENTS

| JP | 2008-086389 A | 4/2008 |
| JP | 2009-285345 A | 12/2009 |
| JP | 2014-533548 A | 12/2014 |
| JP | 2017-113540 A | 6/2017 |
| JP | 2020-127650 A | 8/2020 |
| WO | 2020069031 A1 | 4/2020 |

OTHER PUBLICATIONS

English language translation of the following: Office action dated Jul. 4, 2023 from the JPO in a Japanese patent application No. 2020-166464 corresponding to the instant patent application.

\* cited by examiner

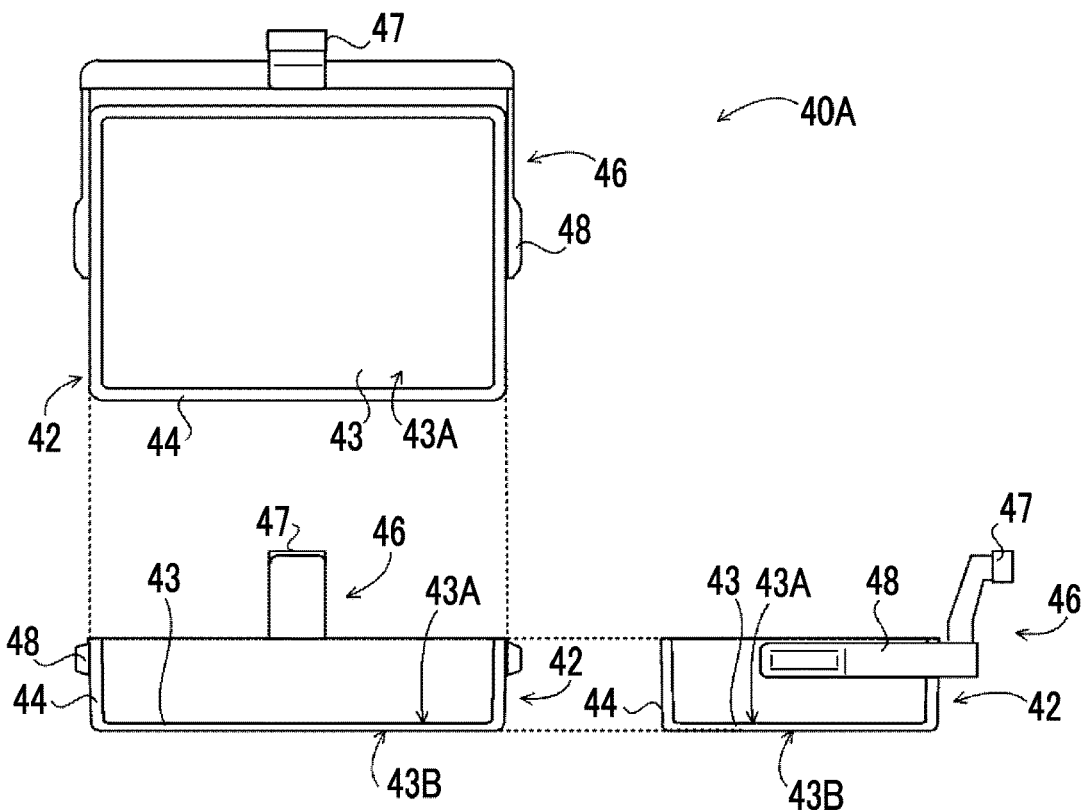
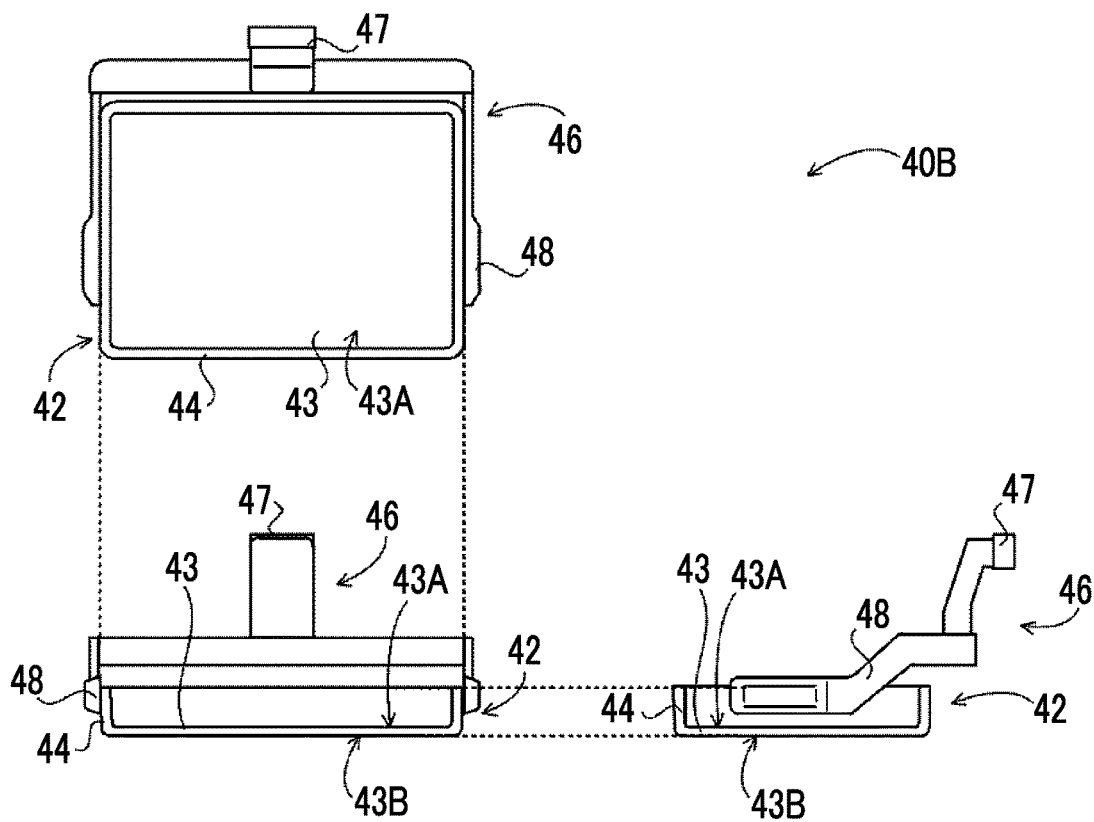

| IDENTIFICATION INFORMATION | PROJECTION SURFACE SIZE INFORMATION | IRRADIATION FIELD |
|---|---|---|
| B001(40A) | 24 × 30 | 24 × 30 |
| B002(40B) | 18 × 24 | 18 × 24 |
| B003(40C) | 10 × 24 | 18 × 24 |
| B004 | 10 × 10 | 9 × 9 |
| ⋮ | ⋮ | ⋮ |

FIG. 13

| IDENTIFICATION INFORMATION | PROJECTION SURFACE SIZE INFORMATION | IRRADIATION FIELD | PROJECTION POSITION INFORMATION | |
|---|---|---|---|---|
| | | | GUIDE INFORMATION | IMAGING INFORMATION |
| B001(40A) | 24 × 30 | 24 × 30 | FIRST PROJECTION SURFACE | UPPER PORTION OF FIRST PROJECTION SURFACE |
| B002(40B) | 18 × 24 | 18 × 24 | FIRST PROJECTION SURFACE | LOWER PORTION OF FIRST PROJECTION SURFACE |
| B003(40C) | 10 × 24 | 18 × 24 | FIRST PROJECTION SURFACE | SECOND PROJECTION SURFACE |
| B004 | 10 × 10 | 9 × 9 | (EITHER) FIRST PROJECTION SURFACE | |
| ... | ... | ... | ... | ... |

53

INFORMATION PROCESSING DEVICE, INFORMATION PROCESSING METHOD, AND INFORMATION PROCESSING PROGRAM

CROSS-REFERENCE TO RELATED APPLICATIONS

The present application claims priority under 35 U.S.C. § 119 to Japanese Patent Application No. 2020-166464, filed on Sep. 30, 2020. The above application is hereby expressly incorporated by reference, in its entirety, into the present application.

BACKGROUND

Technical Field

The present disclosure relates to an information processing device, an information processing method, and an information processing program.

Related Art

In the related art, a radiography apparatus is known which performs radiography for the purpose of medical diagnosis. An example of this type of radiography apparatus is a mammography apparatus that captures the image of the breast of a subject. The mammography apparatus irradiates the breast of the subject which is an imaging part with radiation to capture an image in a state in which the breast is compressed by a compression plate.

In addition, a technique is known which projects an image indicating, for example, the outward shape of the breast onto an imaging table in a mammography apparatus (see, for example, JP2009-285345A). JP2009-285345A describes a technique which projects, on an imaging table, an image of an isobar indicating a compression pressure distribution obtained by detecting compression pressure in the positioning of the breast and an image of the outward shape of the breast.

As described above, a technique is known which projects various kinds of information related to the capture of the breast such that the user can check various kinds of information. However, since various kinds of information are checked by the user in mammography, it may be difficult to project all of the information related to the capture of the image of the breast depending on the size of a projection surface. On the other hand, for example, the information that the user wants to check may differ depending on the work processes (for example, the positioning, compression, imaging, and decompression of the breast) performed in mammography. In addition, the information that the user wants to check may differ depending on the preference of the user. That is, it is considered that it is not necessary to project all of the information related to the capture of the image of the breast onto the projection surface as long as the information that the user wants to check can be projected.

SUMMARY

The present disclosure has been made in view of the above-mentioned problems, and an object of the present disclosure is to provide an information processing device, an information processing method, and an information processing program that can display information desired by a user.

According to a first aspect of the present disclosure, there is provided an information processing device including at least one processor. The processor controls an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

According to a second aspect of the present disclosure, in the first aspect, the processor may receive a selection instruction to select the first information and the second information projected onto the first projection surface and switch the first information and the second information projected onto the first projection surface on the basis of the selection instruction.

According to a third aspect of the present disclosure is, in the above aspects, the processor may switch the first information and the second information projected onto the first projection surface for a period for which the breast is positioned between the radiation source and the radiation detector and a period after the positioning is completed.

According to a fourth aspect of the present disclosure, in the above aspects, the processor may switch the first information and the second information projected onto the first projection surface according to a compression pressure of the breast by the compression member.

According to a fifth aspect of the present disclosure, in the above aspects, the processor may switch the first information and the second information projected onto the first projection surface according to a thickness of the breast in a compression direction in which the breast is compressed.

According to a sixth aspect of the present disclosure, in the above aspects, the processor may acquire projection surface size information indicating a size of the first projection surface and change a relative position of the first information and the second information projected onto the first projection surface depending on the size of the first projection surface indicated by the projection surface size information.

According to a seventh aspect of the present disclosure, in the above aspects, the processor may acquire projection surface size information indicating a size of the first projection surface, perform control to project both the first information and the second information onto the first projection surface in a case in which the projection surface size information indicates that the first projection surface is equal to or larger than a predetermined size, and perform control to project either the first information or the second information onto the first projection surface in a case in which the projection surface size information indicates that the first projection surface is smaller than the predetermined size.

According to an eighth aspect of the present disclosure, in the above aspects, the image projection unit may project an image onto a second projection surface different from the first projection surface of the compression member in addition to the first projection surface, and the processor may control the image projection unit such that the first information and the second information are projected onto different projection surfaces of the first and second projection surfaces.

According to a ninth aspect of the present disclosure, in the above aspects, the processor may perform control to project the first information and the second information in different display aspects.

According to a tenth aspect of the present disclosure, in the aspects, the first information may be guide information that serves as a guide in a case in which the breast is positioned, and the second information may be imaging information including at least one of information indicating a compression pressure of the breast by the compression member, information indicating a thickness of the breast in a compression direction in which the breast is compressed, subject information indicating a subject pertaining to the breast as an object to be imaged, radiographer information indicating a radiographer who performs imaging, date information indicating a date of imaging, or angle information indicating an angle at which an image of the breast is captured.

According to an eleventh aspect of the present disclosure, there is provided an information processing method including controlling an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

According to a twelfth aspect of the present disclosure, there is provided an information processing program that causes a computer to perform a process of: controlling an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

According to the present disclosure, it is possible to display the information desired by the user.

BRIEF DESCRIPTION OF THE DRAWINGS

FIG. 3 is a three-view diagram illustrating an example of a compression plate.

FIG. 4 is a three-view diagram illustrating an example of a compression plate.

FIG. 13 is a diagram illustrating an example of compression plate information according to a second embodiment.

DETAILED DESCRIPTION

Hereinafter, embodiments of the present disclosure will be described in detail with reference to the drawings. In addition, each of the embodiments does not limit the present disclosure.

First Embodiment

Figure 1:
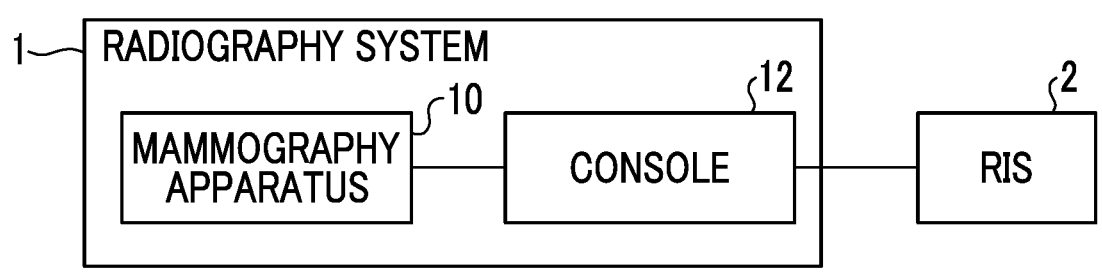
FIG. 1 is a diagram schematically illustrating an example of the overall configuration of a radiography system according to each embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of an information processing device according to the present disclosure.

Figure 2:
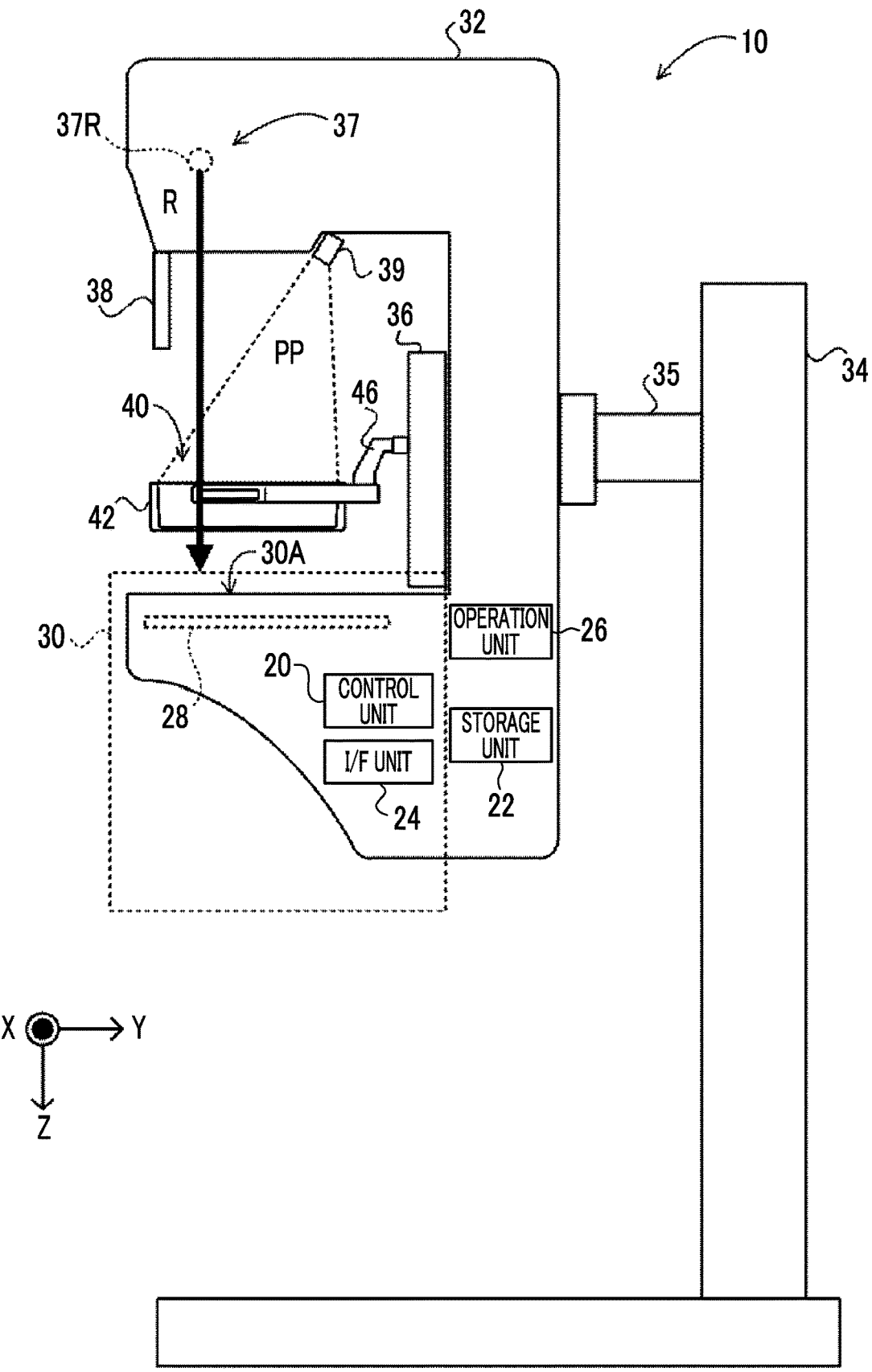
FIG. 2 is a side view illustrating an example of the outward appearance of a mammography apparatus according to each embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD).

The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

The operation unit 26 is provided as plural switches in, for example, the imaging table 30 of the mammography apparatus 10. Further, the operation unit 26 may be provided as a touch panel switch or may be provided as a foot switch that is operated by the user's feet.

As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician. The radiation detector 28 detects the radiation R transmitted through the breast and the imaging table 30, generates a radiographic image on the basis of the detected radiation R, and outputs image data indicating the generated radiographic image. In addition, the type of the radiation detector 28 is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2, the radiation emitting unit 37 is provided in an arm portion 32 together with the imaging table 30 and a compression unit 36. The radiation emitting unit 37 according to this embodiment is configured such that an irradiation field can be changed. The irradiation field may be changed, for example, by the operation of the operation unit 26 by the user or by the control unit 20 according to the type of an attached compression plate 40.

At least one projector 39, which is an example of an image projection unit according to the present disclosure, is provided at a position of the arm portion 32 which is away from the subject below the radiation emitting unit 37. The projector 39 projects a projection image PP onto a projection surface of the compression plate 40 under the control of the console 12. A display image corresponding to the projection image PP is displayed on the projection surface of the compression plate 40 by the projection of the projection image PP by the projector 39. The projection image PP includes at least one of guide information GI or imaging information RI which will be described below. The projection surface is at least one surface that constitutes the compression plate 40. Known projectors, such as a liquid crystal projector, a Digital Light Processing (DLP) (registered trademark) projector, and a laser projector, can be used as the projector 39. In addition, plural projectors 39 that can project the projection image PP onto plural projection surfaces of the compression plate 40 may be provided. Further, for example, a mirror for changing the projection direction of the projector 39 may be provided.

A face guard 38 is attachably and detachably provided at a position of the arm portion 32 which is close to the subject below the radiation emitting unit 37. A face guard 38 is a protective member for protecting the subject from the radiation R emitted from the radiation source 37R.

As illustrated in FIG. 2, the mammography apparatus 10 according to this embodiment comprises the arm portion 32, a base 34, and a shaft portion 35. The arm portion 32 is held by the base 34 so as to be movable in the up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

There are plural types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 for so-called spot imaging that captures a radiographic image of only the region in which a lesion is present is known. Further, other types of compression plates 40 include, for example, a compression plate corresponding to the size of the breast, a compression plate for axillary imaging, and a compression plate for enlargement imaging.

As a specific example, three types of compression plates 40A to 40C that can be attached to the mammography apparatus 10 according to this embodiment will be described with reference to FIGS. 3 to 5, respectively. Hereinafter, in a case in which the compression plates 40A to 40C are generically referred to regardless of the type, they are simply referred to as "compression plates 40".

FIG. 3 is a three-view diagram illustrating an example of the compression plate 40A according to this embodiment. The compression plate 40A is a standard-size compression plate that is mainly used outside Japan. The three-view diagram illustrated in FIG. 3 includes a plan view (top view) of the compression plate 40A viewed from the upper side (from the radiation emitting unit 37), a side view of the compression plate 40A viewed from the subject, and a side view of the compression plate 40A viewed from the right side of the subject. As illustrated in FIG. 3, the compression plate 40A according to this embodiment includes a compression portion 42 and a support portion 46.

The compression portion 42 is formed in a concave shape in a cross-sectional view in which a bottom portion 43 is surrounded by a wall portion 44. In the bottom portion 43, the thickness of a plate having a contact surface 43B that comes into contact with the breast of the subject is substantially constant, and an upper surface 43A that faces the radiation source 37R is flat and has a substantially uniform height. Further, the wall portion 44 is relatively high and has a substantially uniform height.

It is preferable that the compression portion 42 is optically transparent in order to check positioning or a compressed state in the compression of the breast. In addition, the compression portion 42 is made of a material having high transmittance for the radiation R. Specific examples of the material are resins, such as polycarbonate (PC), polyethylene terephthalate (PET), acrylic, and polypropylene (PP). However, the material is not particularly limited.

The support portion 46 is an example of a support member according to the present disclosure and includes an attachment portion 47 and an arm 48. The attachment portion 47 has a function of attaching the compression plate 40 to the mammography apparatus 10, specifically, the compression plate driving unit in the compression plate 40. The arm 48 has a function of supporting the compression portion 42.

FIG. 4 is a three-view diagram illustrating an example of the compression plate 40B according to this embodiment. The compression plate 40B is a compression plate having a smaller size than the compression plate 40A that is mainly used in Japan and is suitable for Japanese people who tend to have smaller breasts than foreigners. The three-view diagram illustrated in FIG. 4 includes a plan view (top view) of the compression plate 40B viewed from the upper side (from the radiation emitting unit 37), a side view of the compression plate 40B viewed from the subject, and a side view of the compression plate 40B viewed from the right side of the subject. As illustrated in FIG. 4, the compression plate 40B according to this embodiment includes a compression portion 42 and a support portion 46, similarly to the compression plate 40A. The compression plate 40B has a smaller bottom portion 43 and a lower wall portion 44 than the compression plate 40A illustrated in FIG. 3. Further, the support portion 46 includes an arm 48 having a different shape. The other configurations are the same as those of the compression plate 40A.

Figure 5:
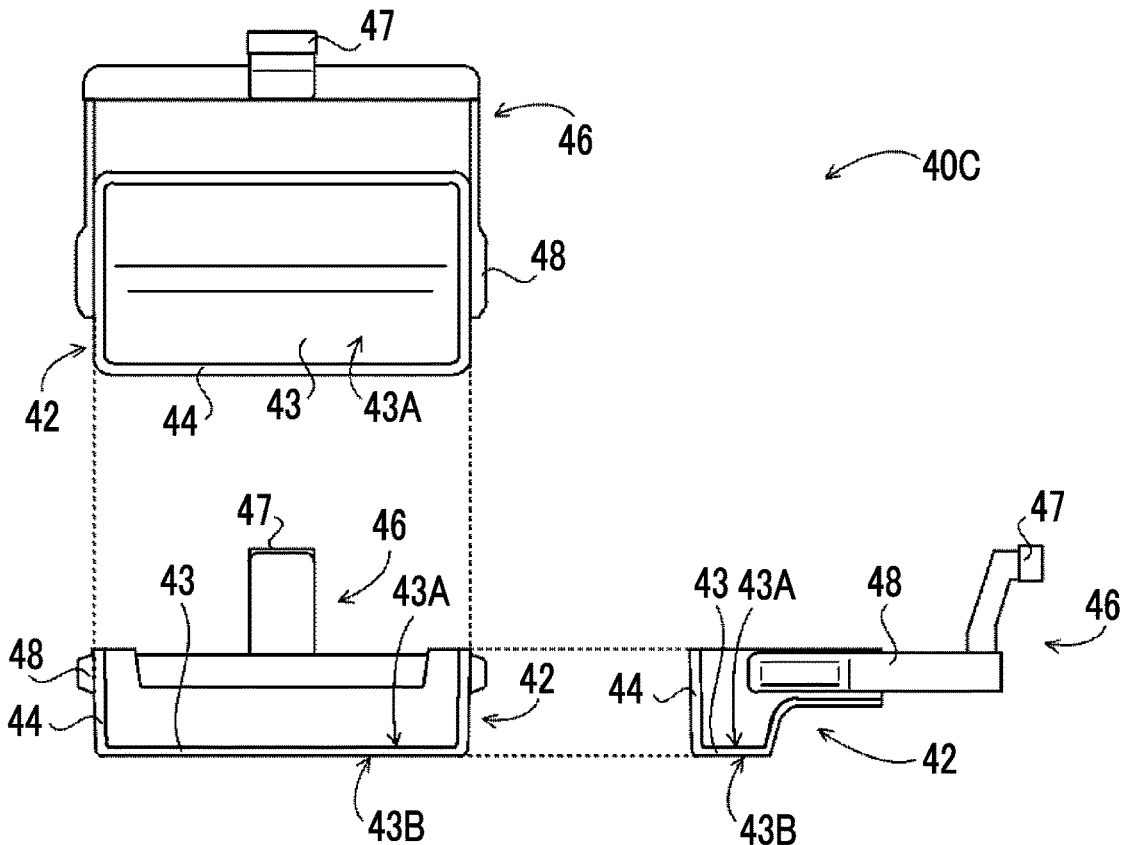
FIG. 5 is a three-view diagram illustrating an example of a compression plate.

FIG. 5 is a three-view diagram illustrating an example of the compression plate 40C according to this embodiment. The compression plate 40C is a compression plate for a small breast and has a shape that makes it easy for a radiographer to position and compress the breast. The three-view diagram illustrated in FIG. 5 includes a plan view (top view) of the compression plate 40C viewed from the upper side (from the radiation emitting unit 37), a side view of the compression plate 40C viewed from the subject, and a side view of the compression plate 40C viewed from the right side of the subject. As illustrated in FIG. 5, the compression plate 40C according to this embodiment includes a compression portion 42 and a support portion 46, similarly to the compression plates 40A and 40B. The compression plate 40C includes a bottom portion 43 which is not flat and in which a part close to an attachment portion 47 is higher than a part close to the chest wall (a part away from the attachment portion 47). Further, the height of a wall portion 44 is not uniform. In the wall portion 44, the height of a part close to the chest wall is lower than the height of the other parts.

In accordance with the above, different types of compression plates 40 are prepared according to, for example, the physique of the subject (for example, the size of the breast) and the type of imaging (for example, enlargement imaging and spot imaging) and can be attached to and detached from the mammography apparatus 10. Therefore, the mammography apparatus 10 according to this embodiment acquires identification information for identifying the type of the compression plate 40.

For example, plural pins whose disposition varies depending on the type of the compression plate 40 may be provided as the identification information in the attachment portion 47 of the compression plate 40, and the identification information may be read by a sensor that can detect the disposition of the pins provided in the mammography apparatus 10. In addition, for example, a detection marker corresponding to the type of the compression plate 40 may be provided as identification information at any position of the compression plate 40, and the identification information may be read by a sensor such as a photointerrupter that can detect each bit of the detection marker provided in the mammography apparatus 10. Further, for example, the mammography apparatus 10 may store a table, in which the identification information of the compression plate 40 and weight are associated with each other, in the storage unit 22 in advance, and the weight of the compression plate 40 measured by a sensor that can detect the weight may be collated with the table to acquire the identification information.

Next, the console 12 according to this embodiment will be described. The console 12 has a function of controlling the mammography apparatus 10 using, for example, an imaging order and various kinds of information acquired from a radiology information system (RIS) 2 through a wireless local area network (LAN) or the like and instructions input by the user through an operation unit 56 or the like.

The imaging order includes, for example, subject information, such as the name, sex, and date of birth of the subject whose image is to be captured, and an imaging item to be captured. For example, the imaging item is the designation of various types of imaging, such as cranio-caudal (CC) imaging, medio-lateral oblique (MLO) imaging, enlargement imaging, and spot imaging, for each of the left and right breasts.

Figure 6:
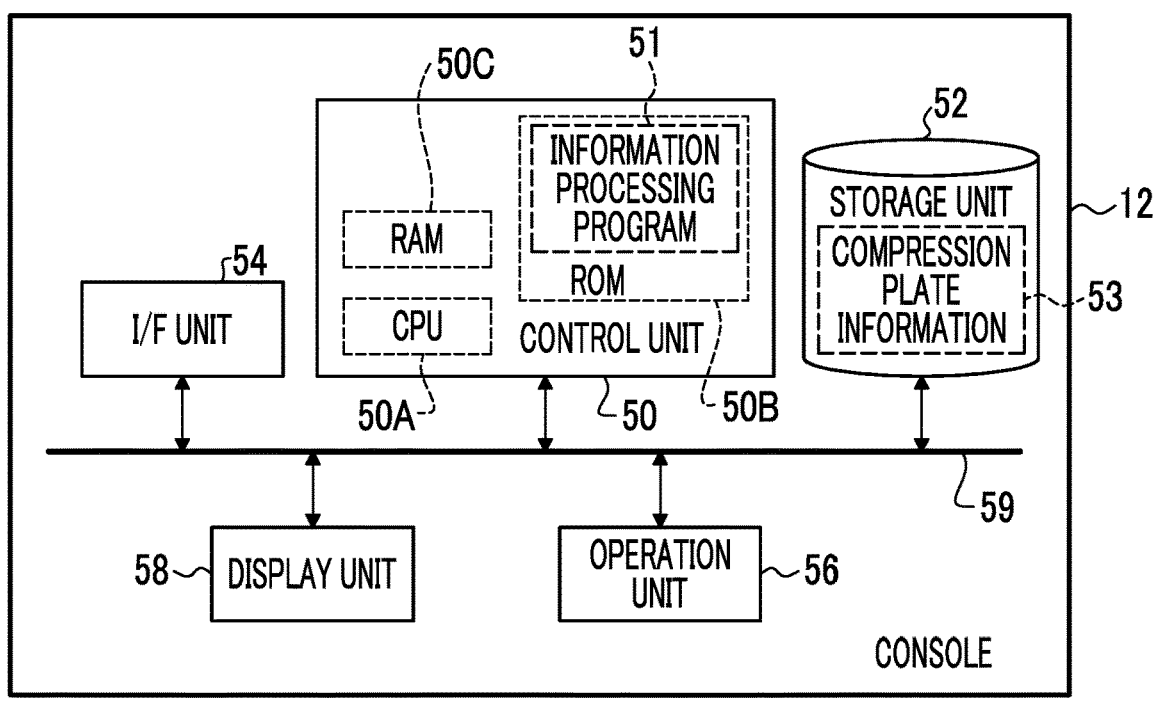
FIG. 6 is a block diagram illustrating an example of the hardware configuration of a console according to each embodiment.

For example, the console 12 according to this embodiment is a server computer. As illustrated in FIG. 6, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an information processing program 51 (which will be described below) executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure.

For example, the image data of the radiographic image captured by the mammography apparatus 10, compression plate information 53, and various other kinds of information are stored in the storage unit 52. An HDD or an SSD is given as a specific example of the storage unit 52. The image data of the radiographic image is stored so as to be associated with the imaging order.

In addition, imaging information is given to the image data of the radiographic image. For example, the imaging information is at least one of subject information indicating the subject pertaining to the breast to be imaged, radiographer information indicating the radiographer who performs imaging, date information indicating the date of imaging, radiographic image size information indicating the size of the radiographic image, or angle information indicating the angle at which the image of the breast is captured. The radiographer is, for example, a user such as a doctor or a radiology technician. The angle at which the image of the breast is captured is represented by, for example, the rotation angle of the arm portion 32 with respect to the base 34, is 0 degrees in the case of CC imaging, and is equal to or greater than 45 degrees and less than 90 degrees in the case of MLO imaging.

Figures 7, 8:
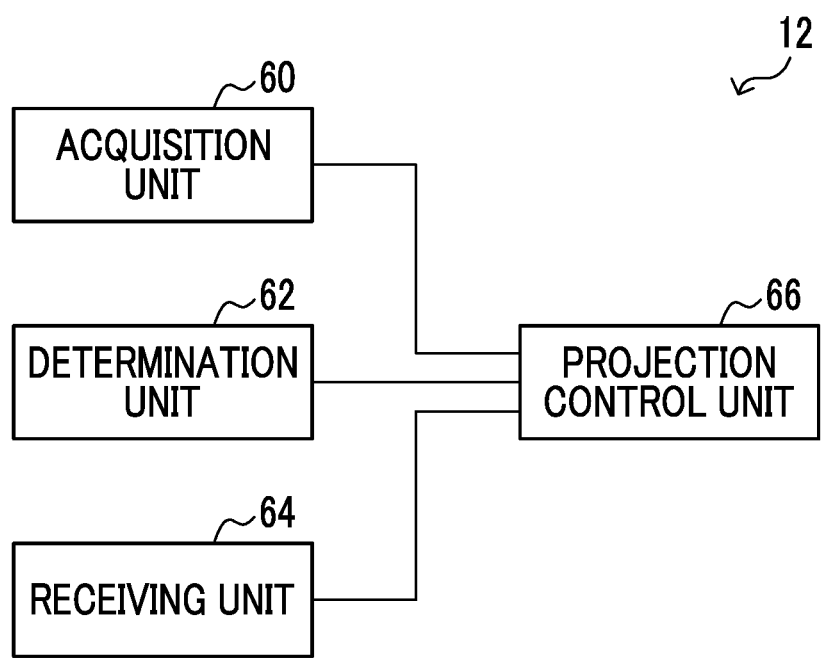
FIG. 7 is a diagram illustrating an example of compression plate information according to a first embodiment.
FIG. 8 is a functional block diagram illustrating an example of the functions of the console according to each embodiment.

FIG. 7 illustrates an example of the compression plate information 53. As illustrated in FIG. 7, the compression plate information 53 includes identification information assigned to each type of compression plate 40, information related to the size of the projection surface of the compression plate 40 (hereinafter, referred to as "projection surface size information"), and the size of the irradiation field suitable for the compression plate 40 which are associated with each other. In FIG. 7, the reference numerals of the corresponding compression plates 40A to 40C are also written in an identification information field.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

As described above, the projector 39 projects the projection image PP including at least one of the guide information GI or the imaging information RI onto the projection surface of the compression plate 40. However, in a case in which both the guide information GI and the imaging information RI are projected onto the projection surface, the information is displayed on the projection surface so as to overlap each other, and visibility may be reduced.

On the other hand, in the mammography, in some cases, the information that the user wants to check may differ depending on work processes such as the positioning of the breast, the compression of the breast, imaging, and the decompression of the breast. For example, it is considered that the user checks positioning guide information in a case in which the breast is positioned and checks the information of compression pressure in a case in which the compression pressure applied to the breast is adjusted. In addition, the information that the user wants to check may differ depending on the preference of the user. That is, it is considered that it is not necessary to project all of the information related to the capture of the image of the breast onto the compression plate as long as the information that the user wants to check can be projected.

Therefore, the console 12 according to this embodiment has a function of controlling the information projected onto the compression plate 40 by the projector 39 so as to be switchable. FIG. 8 is a functional block diagram illustrating an example of the configuration of the console 12 according to this embodiment. As illustrated in FIG. 8, the console 12 comprises an acquisition unit 60, a receiving unit 64, a determination unit 62, and a projection control unit 66. In the console 12 according to this embodiment, the CPU 50A of the control unit 50 executes the information processing program 51 stored in the ROM 50B to function as the acquisition unit 60, the receiving unit 64, the determination unit 62, and the projection control unit 66.

The acquisition unit 60 acquires the guide information GI and the imaging information RI as the information to be projected onto the projection surface of the compression plate 40 by the projector 39. The guide information GI is an example of first information according to the present disclosure, and the imaging information RI is an example of second information according to the present disclosure.

Figure 10:
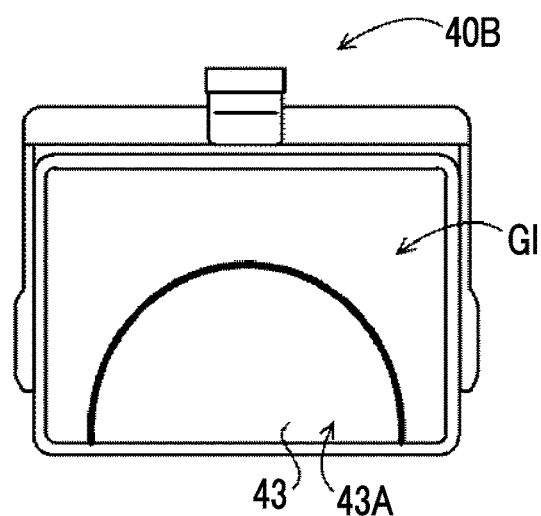
FIG. 10 is a diagram illustrating a compression plate onto which guide information according to the first embodiment is projected.

The guide information GI is information that serves as a guide in a case in which the breast is positioned. FIG. 10 illustrates an example of the compression plate 40B in a state in which the guide information GI is projected onto the projection surface (upper surface 43A). Specifically, the guide information GI may be a skin line image indicating at least a portion of the periphery of the breast in the compressed state as illustrated in FIG. 10, an image indicating the position of the nipple, or the captured radiographic image of the breast in the compressed state.

Figure 11:
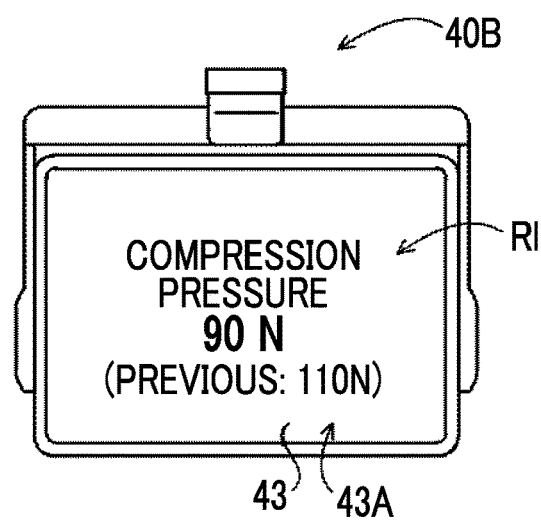
FIG. 11 is a diagram illustrating the compression plate on which imaging information according to the first embodiment is projected.

The imaging information RI is various kinds of information related to the capture of the image of the breast. Specifically, the imaging information RI is information including at least one of information indicating the compression pressure of the breast by the compression plate 40, information indicating the thickness of the breast in a compression direction in which the breast is compressed, subject information indicating the subject pertaining to the breast to be imaged, radiographer information indicating the radiographer who performs imaging, date information indicating the date of imaging, or angle information indicating the angle at which the image of the breast is captured. FIG. 11 illustrates an example of the compression plate 40B in a state in which information indicating the compression pressure of the breast by the compression plate 40 is projected onto the projection surface (upper surface 43A) as an example of the imaging information RI.

In addition, the imaging information RI may be information related to the current imaging or information related to the past imaging. For example, as illustrated in FIG. 11, the imaging information RI may include both the compression pressure in the past imaging ("previous: 110N" in FIG. 11) and the currently measured compression pressure ("90N" in FIG. 11) for the same subject.

The determination unit 62 determines a period (hereinafter, referred to as a "positioning period") for which the breast is positioned between the radiation source 37R and the radiation detector 28 and a period (hereinafter, referred to as a "compression period") after the positioning is completed. The reason is that it is considered that the user often switches the information to be referred to according to the period. For example, the user refers to the guide information GI for the positioning period and refers to the information of the compression pressure applied to the breast by the compression plate 40 for the compression period.

Figure 9:
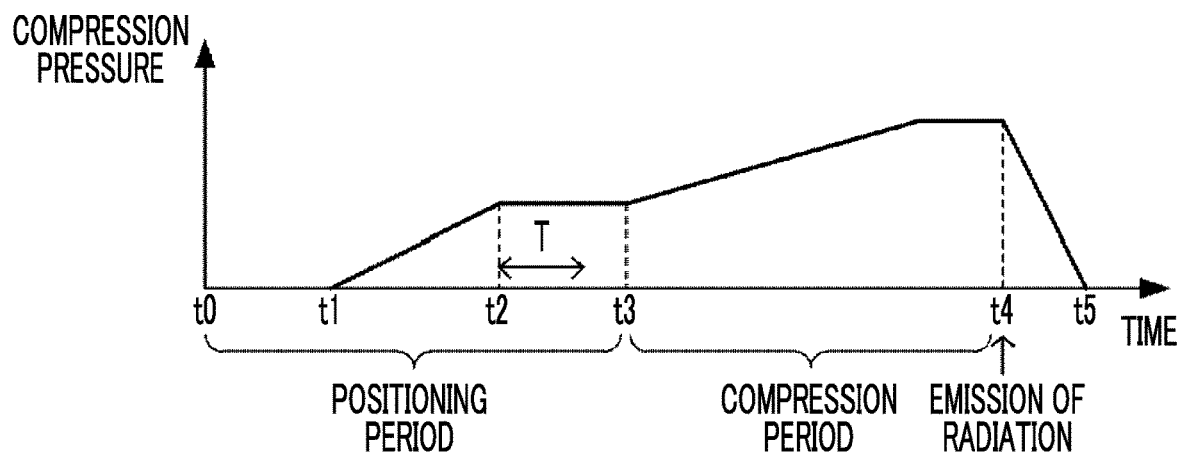
FIG. 9 is a diagram illustrating a determination process of a determination unit.

Specifically, the determination unit 62 determines the positioning period and the compression period according to the compression pressure of the breast by the compression plate 40. An example of a method for determining the positioning period and the compression period according to the compression pressure will be described with reference to FIG. 9. FIG. 9 is a diagram illustrating an example of a change in compression pressure in one mammography operation. In FIG. 9, the horizontal axis indicates time, and the vertical axis indicates the compression pressure applied to the breast. The user determines the rough position of the breast from a time t0 to a time t1, lightly compresses the breast with the compression plate 40 from the time t1 to a time t2, and finely positions the breast from the time t2 to a time t3. Then, the user strongly compresses the breast with the compression plate 40 to expand the mammary glands from the time t3 to a time t4. In this state, the user performs imaging at the time t4 and decompresses the breast from the time t4 to a time t5.

In this case, it can be presumed on the basis of the compression pressure that the positioning is performed for the period (from the time t2 to the time t3 in FIG. 9) for which the compression pressure is constant and the compression is started in a case in which the compression pressure increases. Therefore, the determination unit 62 determines that the period has been switched from the positioning period to the compression period in a case in which the compression pressure increases after it is constant only for a predetermined period T. For example, the period T is predetermined on basis of the time required to position the breast.

In addition, as the compression pressure applied to the breast becomes higher, the thickness of the breast in the compression direction in which the breast is compressed becomes smaller. Therefore, the determination unit 62 may determine the positioning period and the compression period according to the thickness of the breast in the compression direction in which the breast is compressed. The determination unit 62 may perform the determination on the basis of only the thickness of the breast instead of the compression pressure applied to the breast or may combine the compression pressure and the thickness of the breast to perform the determination.

The receiving unit 64 receives a selection instruction to select the guide information GI and the imaging information RI to be projected onto the projection surface. For example, two switches for turning on and off the projection of each of the guide information GI and the imaging information RI may be provided as the operation unit 56, and the user may operate the switches to select the guide information GI and the imaging information RI to be projected onto the projection surface. That is, the selection instruction can take four states, that is, a state in which both the guide information GI and the imaging information RI are projected, a state in which only the guide information GI is projected, a state in which only the imaging information RI is projected, and a state in which neither the guide information GI nor the imaging information RI is projected.

The projection control unit 66 performs control to project the guide information GI and the imaging information RI onto the projection surface of the compression plate 40 so as to be switchable. Specifically, the projection control unit 66 switches the guide information GI and the imaging information RI projected onto the projection surface according to the period determined by the determination unit 62 and the selection instruction received by the receiving unit 64. For example, in a case in which both the guide information GI and the imaging information RI are selected by the selection instruction, the projection control unit 66 performs control to project the guide information GI for the positioning period (see FIG. 10) and to project the imaging information RI for the compression period (see FIG. 11). On the other hand, in a case in which either the guide information GI or the imaging information RI is selected by the selection instruction, the projection control unit 66 performs control to project only the selected information for the entire period regardless of the period determined by the determination unit 62. In addition, in a case in which neither the guide information GI nor the imaging information RI is selected by the selection instruction, the projection control unit 66 may perform control not to project any information.

Figure 15:
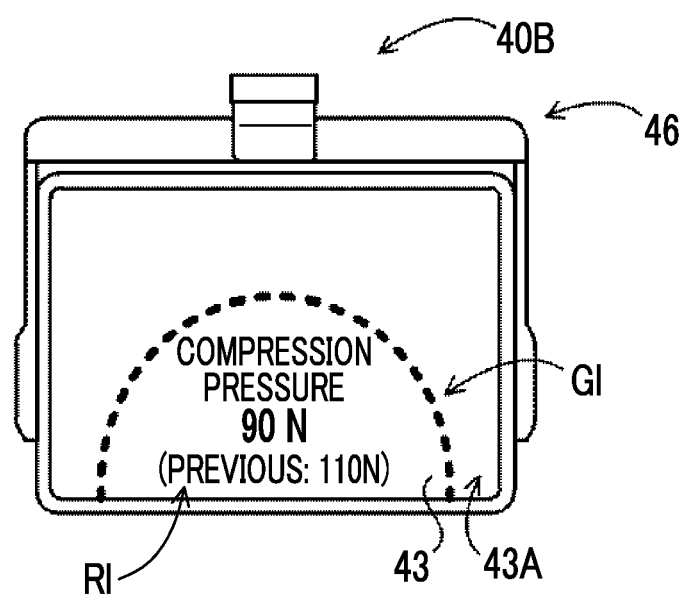
FIG. 15 is a diagram illustrating a compression plate onto which the guide information and the imaging information according to the second embodiment are projected.

Further, the projection control unit 66 may perform control to project the guide information GI and the imaging information RI in different display aspects (see FIG. 15). The display aspect includes, for example, a line type (a solid line, a broken line, and the like), a line thickness, and a line color in the guide information GI and the imaging information RI.

Figure 12:
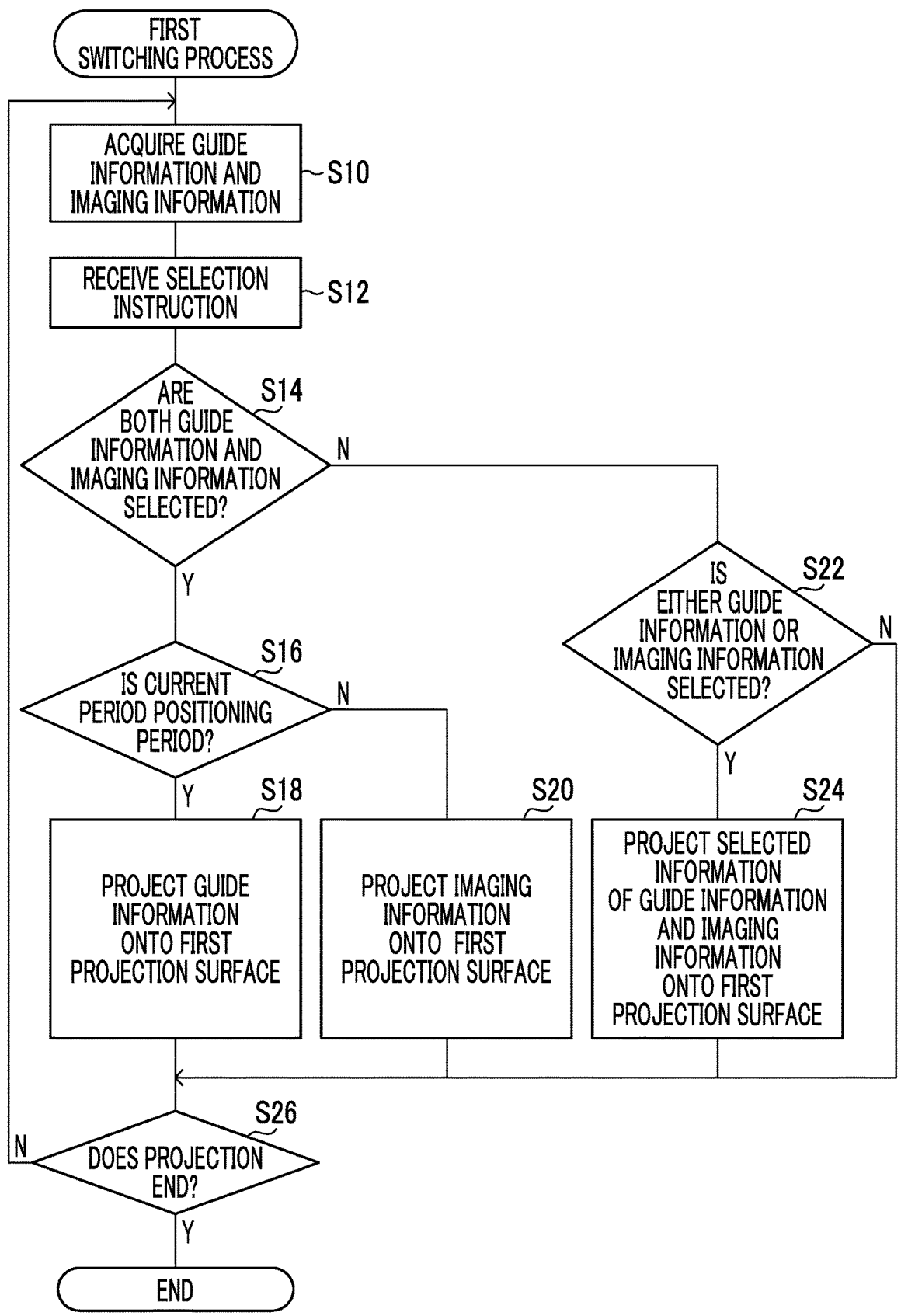
FIG. 12 is a flowchart illustrating an example of the flow of a first switching process in the console according to the first embodiment.

Next, the operation of the console 12 according to this embodiment will be described with reference to FIG. 12. For example, in a case in which the console 12 receives an imaging order from the RIS 2 or the like, the CPU 50A of the control unit 50 executes the information processing program 51 stored in the ROM 50B to perform a first switching process whose example is illustrated in FIG. 12. FIG. 12 is a flowchart illustrating an example of the flow of the first switching process performed in the console 12 according to this embodiment. The first switching process is an example of information processing according to the present disclosure.

In Step S10 of FIG. 12, the acquisition unit 60 acquires the guide information GI and the imaging information RI. In Step S12, the receiving unit 64 receives a selection instruction to select the guide information GI and the imaging information RI to be projected onto the projection surface.

In a case in which both the guide information GI and the imaging information RI are selected by the selection instruction received in Step S12 (Yin Step S14), the process proceeds to Step S16. In Step S16, the determination unit 62 determines whether the current period is the positioning period or the compression period. In a case in which the current period is the positioning period (Yin Step S16), in Step S18, the projection control unit 66 performs control to project only the guide information GI acquired in Step S10 onto the projection surface of the compression plate 40. On the other hand, in a case in which the current period is not the positioning period, but is the compression period (N in Step S16), in Step S20, the projection control unit 66 performs control to project only the imaging information RI acquired in Step S10 onto the projection surface of the compression plate 40.

On the other hand, in a case in which neither the guide information GI nor the imaging information RI is selected by the selection instruction received in Step S12 (N in Step S14), but either the guide information GI or the imaging information RI is selected by the selection instruction (Step S22 is Y), the process proceeds to Step S24. In Step S24, the projection control unit 66 performs control to project the information selected by the selection instruction received in Step S12 of the guide information GI and the imaging information RI acquired in Step S10 onto the projection surface of the compression plate 40.

In a case in which Steps S18, S20, and S24 end and in a case in which neither the guide information GI nor the imaging information RI is selected by the selection instruction received in Step S12 (N in Step S22), the process proceeds to Step S26. In Step S26, the projection control unit 66 determines whether or not to end the projection. In a case in which the projection is continued (N in Step S26), the process returns to Step S10. On the other hand, in a case in which the projection is ended (Yin Step S26), this process ends. In addition, it is determined that the projection is ended at a predetermined timing such as the operation of the operation unit 56 by the user and the completion of the imaging.

As described above, the console 12 according to this embodiment comprises the CPU 50A which is at least one processor. The CPU 50A controls the projector 39 which projects the projection image PP onto the projection surface of the compression plate 40 in the mammography apparatus 10 that irradiates the breast compressed by the compression plate 40 disposed between the radiation source 37R and the radiation detector 28 with the radiation R to capture a radiographic image such that at least one of the first information (guide information GI) or the second information (imaging information RI) is projected onto the projection surface so as to be switchable. That is, according to the console 12 of this embodiment, since at least one of the first information or the second information is switched and projected, it is possible to display the information desired by the user on the compression plate 40.

In addition, in the above-described embodiment, the example has been described in which the radiographer performs imaging in the procedure of positioning the breast and then compressing the breast. However, the technology of the present disclosure can be applied to mammography that is performed in any procedure. For example, the technology of the present disclosure can be applied to a case in which the radiographer compresses the breast and then repositions the breast (that is, the repetition of the positioning period and the compression period). Further, for example, the technology of the present disclosure can be applied to a case in which the radiographer performs the positioning and compression of the breast in parallel and completes the positioning and compression of the breast substantially at the same time (that is, the positioning period and the compression period overlap each other and are not clearly separated). Furthermore, for example, the technology of the present disclosure can be applied to a case in which the breast is compressed by the radiographer's hand in the positioning period and is compressed by the compression plate 40 (that is, the compression pressure is greater than 0) only in the compression period after the positioning is completed. Even in these cases, the console 12 can appropriately switch the information projected onto the projection surface according to at least one of the compression pressure of the breast by the compression plate 40 or the thickness of the breast. Specifically, for example, the console 12 may perform control to switch the information to be projected onto the projection surface in a case in which at least one of the compression pressure of the breast by the compression plate 40 or the thickness of the breast is constant only for a predetermined period. For example, in a case in which the compression pressure of the breast by the compression plate 40 is constant only for a predetermined period, the information projected onto the projection surface may be switched from the guide information GI to the imaging information RI.

In addition, in the above-described embodiment, the aspect has been described in which the determination unit 62 determines that the period has been switched from the positioning period to the compression period in a case in which the compression pressure increases after the compression pressure is constant only for a predetermined period T. However, the present disclosure is not limited thereto. For example, the determination unit 62 may determine that the period has been switched from the positioning period to the compression period in a case in which the compression pressure is greater than a predetermined threshold value. In this case, since appropriate compression pressure changes depending on, for example, the shape and state of the breast, it is preferable to change the threshold value depending on the shape and state of the breast.

Further, in the above-described embodiment, the aspect has been described in which the determination unit 62 determines the positioning period and the compression period according to at least one of the compression pressure of the breast by the compression plate 40 or the thickness of the breast. However, the present disclosure is not limited thereto. For example, the determination unit 62 may determine the positioning period and the compression period in a case in which the user operates the operation unit 56 to notify the start of the compression of the breast (the completion of positioning).

Further, in the above-described embodiment, which of the period determined by the determination unit 62 and the selection instruction received by the receiving unit 64 is prioritized by the projection control unit 66 to switch the guide information GI and the imaging information RI projected onto the projection surface is not particularly limited. For example, in a case in which priority is given to the selection instruction as described in the first switching process and the receiving unit 64 receives the selection instruction, the projection control unit 66 may perform control to project information corresponding to the selection instruction. Furthermore, for example, the selection instruction may be canceled at a predetermined timing, and priority may be given to the period determined by the determination unit 62. The predetermined timing is, for example, the timing when the period determined by the determination unit 62 is switched (the timing when the period is switched from the positioning period to the compression period) and the timing when a predetermined period has elapsed since the receiving unit 64 received the selection instruction.

In addition, in the above-described embodiment, the aspect in which the projection control unit 66 switches the information to be projected according to both the selection instruction received by the receiving unit 64 and the period determined by the determination unit 62 has been described. However, the present disclosure is not limited thereto. For example, the projection control unit 66 may switch the information to be projected according to only one of the selection instruction received by the receiving unit 64 and the period determined by the determination unit 62. In this case, in the console 12, the functions of either the receiving unit 64 or the determination unit 62 may be omitted.

Further, in the above-described embodiment, the aspect in which the projection control unit 66 switches whether or not to project each of the guide information GI and the imaging information RI has been described. However, the present disclosure is not limited thereto. For example, the projection control unit 66 may always project one of the guide information GI and the imaging information RI and may switch the on and off of the projection of the other on the basis of the period determined by the determination unit 62 and the selection instruction received by the receiving unit 64.

Further, in the above-described embodiment, information indicating the height of the compression plate 40 may be used instead of the information indicating the thickness of the breast in the compression direction in which the breast is compressed. The height of the compression plate 40 may be represented by, for example, the distance between the imaging surface 30A (imaging table 30) and the contact surface 43B (the bottom portion 43 of the compression plate 40), the distance between the radiation source 37R and the contact surface 43B (the bottom portion 43 of the compression plate 40), and the amount of driving of the compression plate driving unit from the reference position.

Second Embodiment

A console 12 according to this embodiment has a function of changing the projection positions of the guide information GI and the imaging information RI depending on the size of the projection surface of the compression plate 40. For example, in some cases, the guide information GI and the imaging information RI are projected in a layout suitable for the size of the projection surface, which makes it possible to project a larger amount of information onto the projection surface. Hereinafter, the same configurations as those in the first embodiment are denoted by the same reference numerals, and the description thereof will not be repeated.

Figure 16:
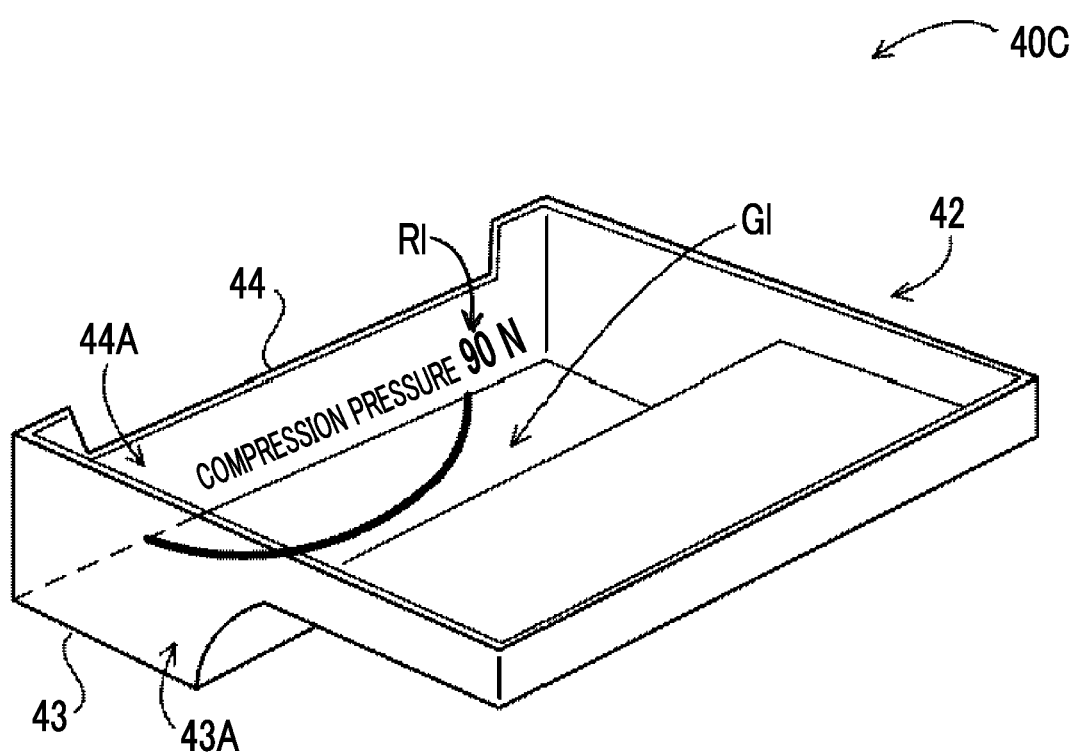
FIG. 16 is a diagram illustrating a compression plate onto which the guide information and the imaging information according to the second embodiment are projected.

A projector 39 according to this embodiment is configured to project the guide information GI and the imaging information RI on plural different projection surfaces (see FIG. 16). Hereinafter, in the following description, the upper surface 43A of the bottom portion 43 of the compression plate 40 is referred to as a first projection surface, and an inner surface 44A of the wall portion 44 of the compression plate 40 is referred to as a second projection surface.

As illustrated in FIG. 13, compression plate information 53 according to this embodiment includes identification information assigned to each type of the compression plate 40, projection surface size information of the first projection surface of the compression plate 40, the size of the irradiation field suitable for the compression plate 40, and projection position information which are associated with each other. The projection position information is information in which the projection position of each of the guide information GI and the imaging information RI is predetermined for each type of the compression plate 40 (that is, for each size of the first projection surface).

The acquisition unit 60 acquires the projection surface size information indicating the size of the first projection surface and the projection position information in addition to the guide information GI and the imaging information RI. Specifically, the acquisition unit 60 acquires the identification information of the compression plate 40 identified by the mammography apparatus 10, collates the identification information with the compression plate information 53 (see FIG. 13) in the storage unit 52, and acquires the projection surface size information corresponding to the compression plate 40 attached to the mammography apparatus 10 and the projection position information.

The projection control unit 66 changes the relative position of the guide information GI and the imaging information RI projected onto the first projection surface according to the size of the first projection surface indicated by the projection surface size information acquired by the acquisition unit 60. Specifically, the projection control unit 66 performs control to project the guide information GI and the imaging information RI at the position based on the projection position information predetermined for each type of the compression plate 40, that is, for each size of the first projection surface.

Figure 14:
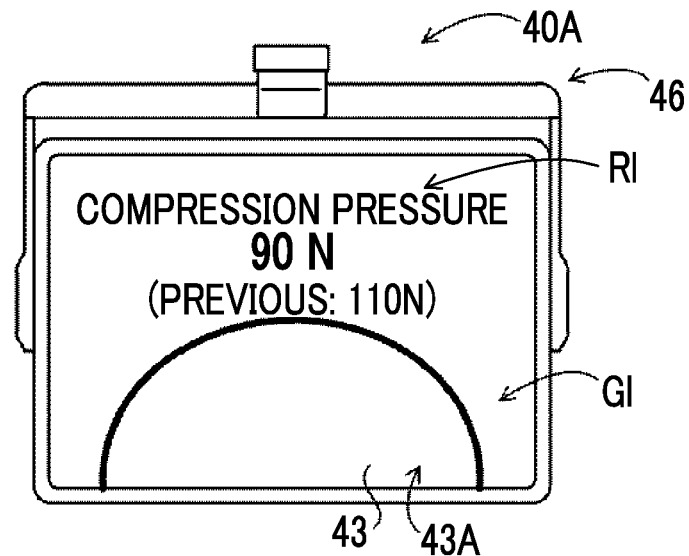
FIG. 14 is a diagram illustrating a compression plate onto which guide information and imaging information according to the second embodiment are projected.

FIG. 14 is a diagram illustrating a state in which the guide information GI and the imaging information RI are projected onto the first projection surface (upper surface 43A) of the compression plate 40A. As illustrated in FIG. 13, in the projection position information corresponding to the compression plate 40A (identification information B001), the projection position of the guide information GI indicates the first projection surface, and the projection position of the imaging information RI indicates an upper portion of the first projection surface (the side opposite to the chest wall of the subject). The projection control unit 66 controls the projector 39 such that the guide information GI is projected onto the first projection surface and the imaging information RI is projected onto the upper portion of the first projection surface on the basis of the projection position information.

FIG. 15 is a diagram illustrating a state in which the guide information GI and the imaging information RI are projected onto the first projection surface (upper surface 43A) of the compression plate 40B. As illustrated in FIG. 13, in the projection position information corresponding to the compression plate 40B (identification information B002), the projection position of the guide information GI indicates the first projection surface, and the projection position of the imaging information RI indicates a lower portion of the first projection surface (the chest wall side of the subject). The projection control unit 66 controls the projector 39 such that the guide information GI is projected onto the first projection surface and the imaging information RI is projected onto the lower portion of the first projection surface on the basis of the projection position information. In addition, in the example illustrated in FIG. 15, since the guide information GI and the imaging information RI are likely to overlap each other, the projection control unit 66 performs control to project the guide information GI and the imaging information RI in different display aspects.

Further, in a case in which the projection surface size information indicates that the first projection surface is equal to or larger than a predetermined size, the projection control unit 66 may perform control to project both the guide information GI and the imaging information RI onto the first projection surface. In a case in which the projection surface size information indicates that the first projection surface is smaller than the predetermined size, the projection control unit 66 may perform control to project either the guide information GI or the imaging information RI onto the first projection surface. For example, the reason is that, in the compression plate 40 having a relatively small first projection surface, it may be inappropriate to project the guide information GI and the imaging information RI onto one projection surface.

In addition, in a case in which the projection surface size information indicates that the first projection surface is smaller than the predetermined size, which of the guide information GI and the imaging information RI is projected may be determined by the method disclosed in the first embodiment. That is, the projection control unit 66 may control the information to be projected on the basis of the period determined by the determination unit 62 and the selection instruction received by the receiving unit 64.

Further, the projection control unit 66 may control the projector 39 such that the guide information GI and the imaging information RI are projected onto different projection surfaces of the first and second projection surfaces. For example, as described above, in a case in which the first projection surface is smaller than the predetermined size and one of the guide information GI and the imaging information RI is projected onto the first projection surface, the other may be projected onto the second projection surface.

FIG. 16 is a diagram illustrating a state in which the guide information GI and the imaging information RI are projected onto the first projection surface (upper surface 43A) and the second projection surface (inner surface 44A) of the compression plate 40C, respectively (the support portion 46 is not illustrated). As illustrated in FIG. 13, in the projection position information corresponding to the compression plate 40C, the projection position of the guide information GI indicates the first projection surface, and the projection position of the imaging information RI indicates the second projection surface. The projection control unit 66 controls the projector 39 such that the guide information GI is projected onto the first projection surface and the imaging information RI is projected onto the second projection surface on the basis of the projection position information.

Figure 17:
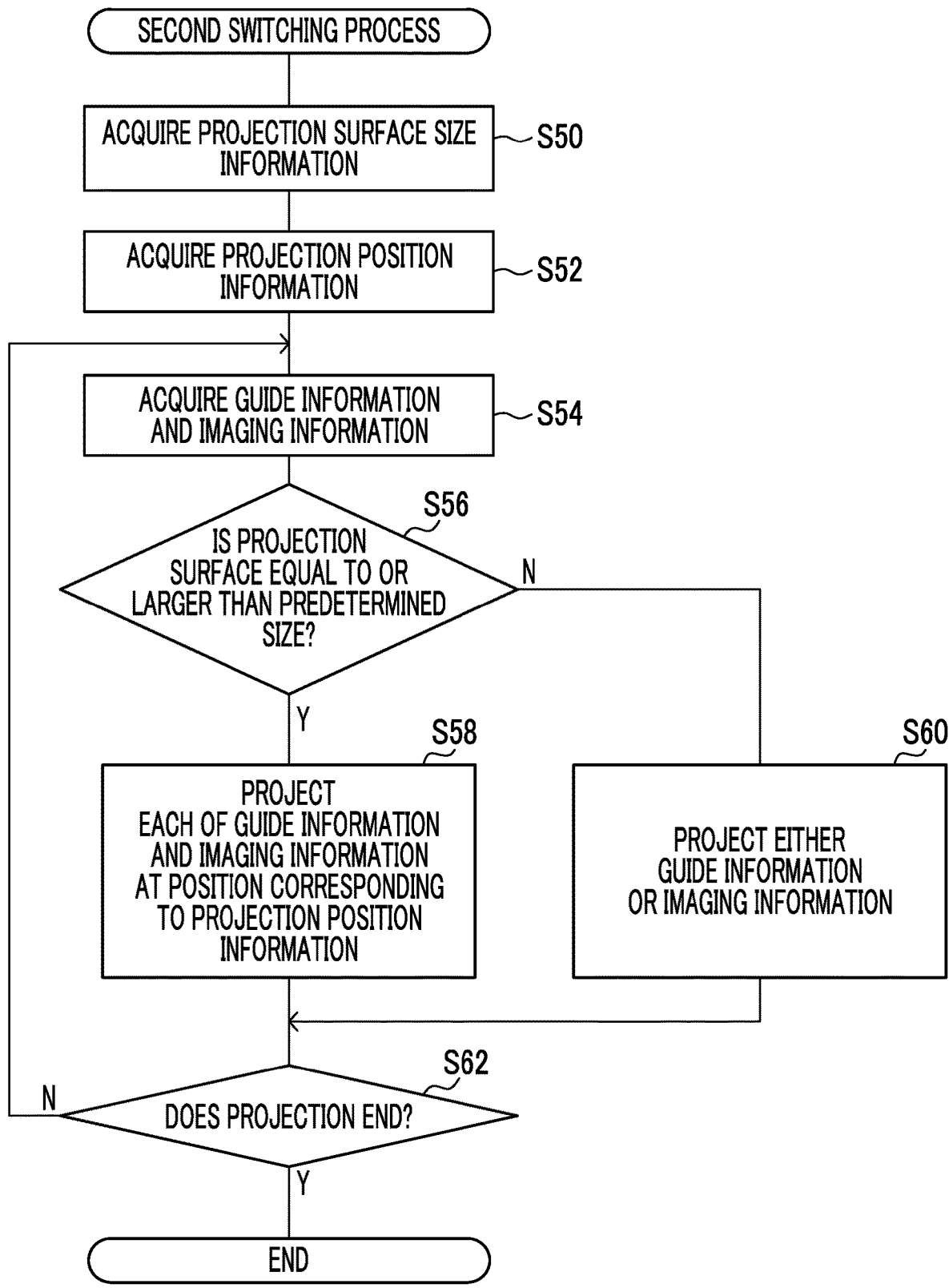
FIG. 17 is a flowchart illustrating an example of the flow of a second switching process in a console according to the second embodiment.

Next, the operation of the console 12 according to this embodiment will be described with reference to FIG. 17. For example, in a case in which the console 12 receives an imaging order from the RIS 2 or the like, the CPU 50A of the control unit 50 executes the information processing program 51 stored in the ROM 50B to perform a second switching process whose example is illustrated in FIG. 17. FIG. 17 is a flowchart illustrating an example of the flow of the second switching process performed in the console 12 according to this embodiment. The second switching process is an example of the information processing according to the present disclosure.

In Step S50 of FIG. 17, the acquisition unit 60 acquires the projection surface size information indicating the size of the first projection surface. In Step S52, the acquisition unit 60 acquires the projection position information. In Step S54, the acquisition unit 60 acquires the guide information GI and the imaging information RI.

In Step S56, the projection control unit 66 determines whether or not the size of the first projection surface indicated by the projection surface size information acquired in Step S50 is equal to or larger than a predetermined size. In a case in which the size of the first projection surface is equal to or larger than the predetermined size (Yin Step S56), in Step S58, the projection control unit 66 performs control to project the guide information GI and the imaging information RI at the position corresponding to the projection position information acquired in Step S52 on the first projection surface. On the other hand, in a case in which the size of the first projection surface is smaller than the predetermined size (N in Step S56), in Step S60, the projection control unit 66 performs control to project either the guide information GI or the imaging information RI onto the first projection surface.

In a case in which Steps S58 and S60 end, in Step S62, the projection control unit 66 determines whether or not to end the projection. In a case in which the projection is continued (N in Step S62), the process returns to Step S54. On the other hand, in a case in which the projection is ended (Yin Step S62), the process ends. In addition, it is determined that the projection is ended at a predetermined timing such as the operation of the operation unit 56 by the user and the completion of the imaging.

As described above, the console 12 according to this embodiment comprises the CPU 50A which is at least one processor. The CPU 50A acquires the projection surface size information indicating the size of the first projection surface and changes the relative position of the guide information GI and the imaging information RI projected onto the first projection surface according to the size of the first projection surface indicated by the projection surface size information. Therefore, it is possible to display a larger amount of information desired by the user on the compression plate 40.

Further, in the above-described embodiment, in a case in which it is determined that the size of the first projection surface of the compression plate 40 indicated by the acquired projection surface size information is smaller than the predetermined size, the acquisition unit 60 may stop the subsequent projection process. The reason is that, for example, in a case in which the attached compression plate 40 is a small compression plate for spot imaging, it is difficult to project the guide information GI and the imaging information RI.

Configuration of Compression Plate 40 Capable of Projecting Light

The configuration of the compression plate 40 onto which the projection image PP can be projected by the projector 39 will be described as a configuration common to the first and second embodiments with reference to FIGS. 18 to 22. As described above, in this embodiment, the compression portion 42 of the compression plate 40 is configured to include a material that is optically transparent in order to perform positioning and to check the compressed state in the compression of the breast. In a case in which light is incident on a transparent object, most (for example, 90%) of the light is transmitted, and a portion (for example, 10%) of the light is specularly reflected from the surface of the object such that an incident angle and a reflection angle are equal to each other. In practice, light absorption occurs in the object, and scattering occurs at the interface of the object and in the object. However, they are ignored here. Light reflected from the surface of the object enters the eyes, and the observer can see light projected onto the surface of the object. That is, even in the compression plate 40 configured to include a transparent material, in a case in which the projection image PP projected by the projector 39 is reflected from the projection surface of the compression plate 40 and the reflected light enters the eyes of the observer, the observer can visually recognize the image displayed on the projection surface.

Figure 18:
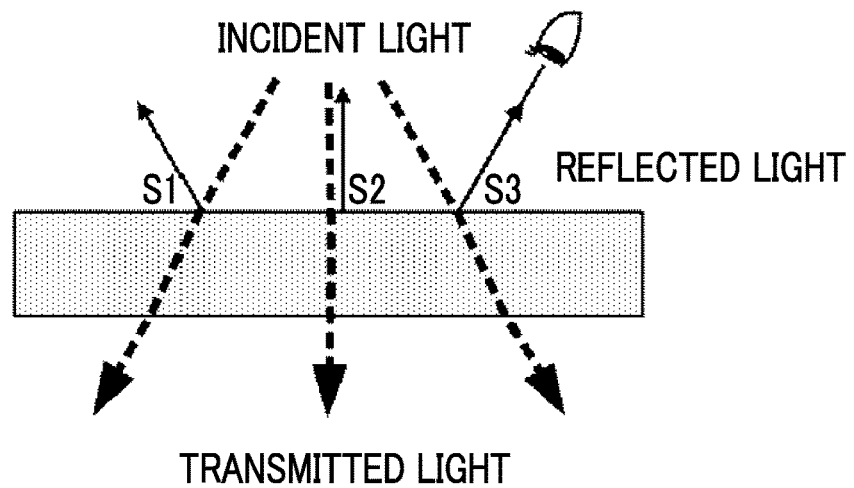
FIG. 18 is a diagram illustrating the principle of reflection from a smooth flat surface.
Figure 19:
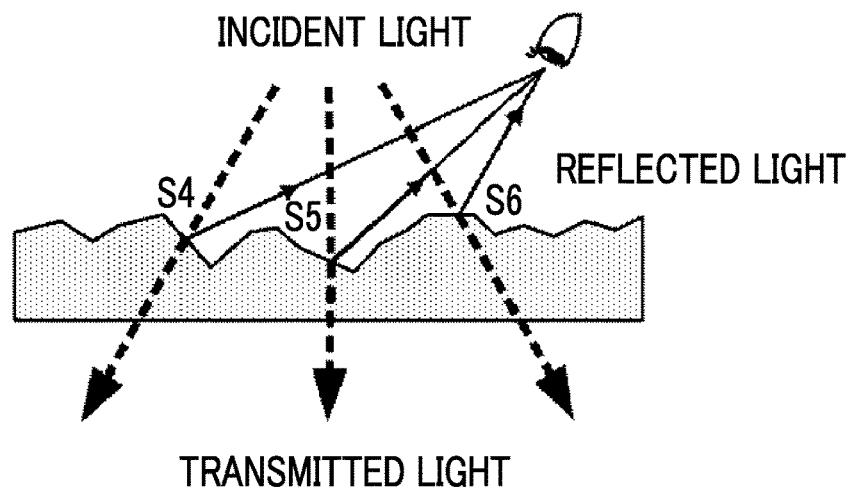
FIG. 19 is a diagram illustrating the principle of reflection from a roughened surface.
Figure 20:
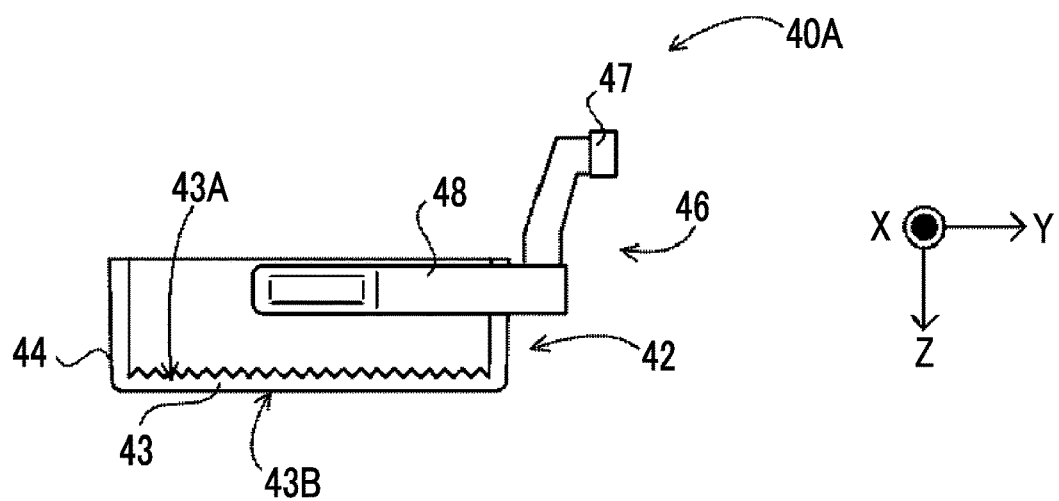
FIG. 20 is a diagram schematically illustrating an example of a compression plate having a roughened projection surface.

FIG. 18 is a diagram illustrating an example of the direction of the reflected light in a case in which incident light is incident on a smooth flat surface. FIG. 19 is a diagram illustrating an example of the direction of the reflected light in a case in which incident light is incident on an uneven surface. In FIGS. 18 and 19, three incident light components are illustrated as representatives. As illustrated in FIGS. 18 and 19, light incident on each of positions S1 to S6 on the surface of the object is specularly reflected, regardless of whether the surface of the object is a smooth flat surface or an uneven surface.

As illustrated in FIG. 18, in a case in which the surface of the object is a smooth flat surface, among the reflected light components at the positions S1 to S3, only the reflected light at the position S3 where the angle (incident angle) with respect to the light source and the angle (reflection angle) with respect to the eyes are equal to each other enters the eyes of the observer. In the eyes of the observer, light is displayed only at the position S3 on the surface of the object and is not displayed at the other positions S1 and S2. That is, in a case in which the projection surface of the compression plate 40 is a smooth flat surface, a display image is not displayed on the projection surface even though the projection image PP is projected onto the projection surface by the projector 39.

On the other hand, as illustrated in FIG. 19, in a case in which the surface of the object is an uneven surface and the angles of the reflecting surfaces at the positions S4 to S6 are different, the angle (incident angle) with respect to the light source and the angle (reflection angle) with respect to the eyes can be equal to each other at each of the positions S4 to S6. In this case, since the reflected light from the positions S4 to S6 enters the eyes of the observer, light is displayed at each of the positions S4 to S6 on the surface of the object in the eyes of the observer. That is, in a case in which the projection surface of the compression plate 40 is an uneven surface and the projection image PP is projected onto the projection surface by the projector 39, the display image is displayed on the projection surface.

Therefore, it is preferable to perform a roughening process on the projection surface of the compression plate 40 in this embodiment such that the observer can visually recognize the display image in a case in which the projection image PP is projected by the projector 39. The roughening process is a process that forms unevenness on the surface of the projection surface. Examples of the roughening process include a surface texturing process and a satin finishing process. A roughening method is not particularly limited, and various known methods, such as a mechanical roughening process, an electrochemical roughening process, and a chemical roughening process, may be used.

Specifically, at least a partial region of at least one surface of the compression plate 40 which does not come into contact with the breast and onto which the projection image PP can be projected by the projector 39 is roughened. For example, in a case in which the skin line image is projected so as to be superimposed on the breast, at least a partial region of the surface (the upper surface 43A of the bottom portion 43 in FIG. 20) which is opposite to the contact surface 43B with the breast is roughened as illustrated in a schematic diagram of FIG. 20. In addition, even in a case in which the contact surface 43B of the bottom portion 43 with the breast is roughened, the display image is displayed on the bottom portion 43. However, it is desirable that the contact surface 43B with the breast is not roughened in order to suppress discomfort caused by the contact of the unevenness with the skin of the subject.

Figure 21:
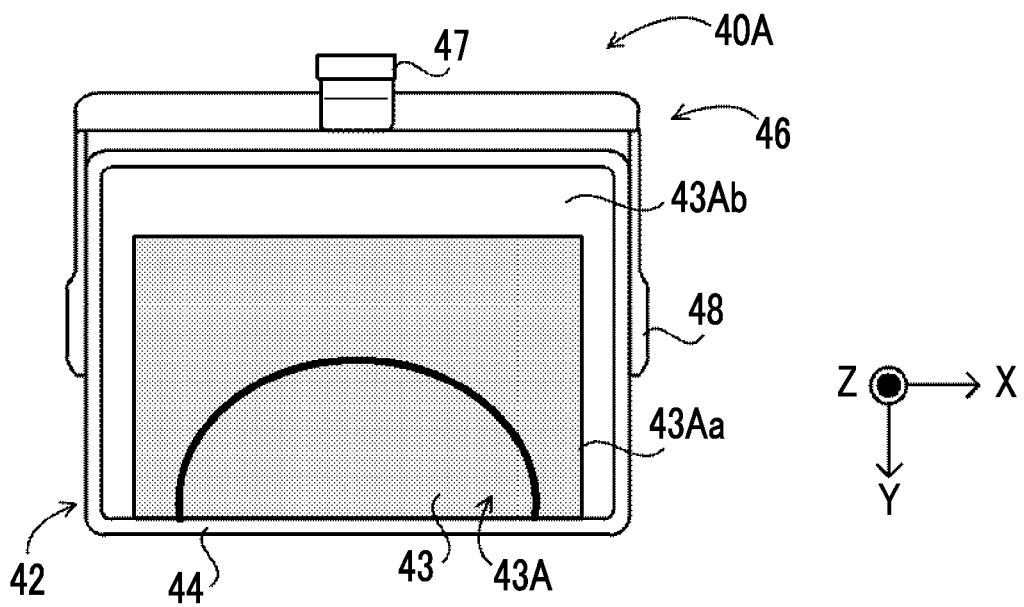
FIG. 21 is a diagram schematically illustrating an example of a compression plate in which a partial region of a projection surface is roughened.
Figure 22:
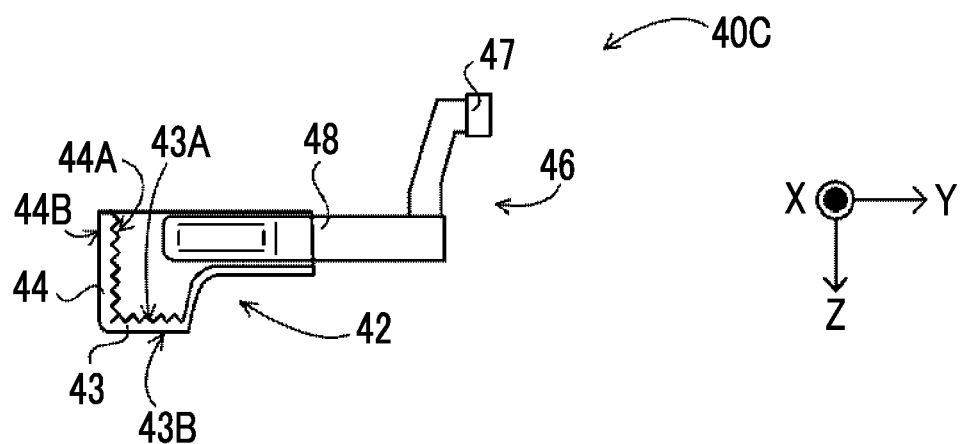
FIG. 22 is a diagram schematically illustrating an example of a compression plate having a roughened projection surface.

Further, assuming that the skin line image is projected so as to be superimposed on the breast, a skin line image projection region is limited to a region on the chest wall side in the upper surface 43A of the compression plate 40. Therefore, for example, as illustrated in FIG. 21, on the surface (the upper surface 43A in FIG. 21) opposite to the contact surface 43B with the breast, a region 43Aa on the chest wall side (the lower side in the Y direction in FIG. 21) may be roughened, and a region 43Ab on the side (the upper side in the Y direction in FIG. 21) opposite to the chest wall may not be roughened. For the same reason, particularly, in the compression plate 40 used for CC imaging, a partial region including the center of the breast in the left-right direction (the X direction in FIG. 21) may be roughened, and the end parts of the breast in the left-right direction (the X direction in FIG. 21) may not be roughened.

Further, for example, in a case in which the projection image PP can be projected onto plural surfaces, at least a partial region of each of the plurality of surfaces that do not come into contact with the breast may be roughened. For example, in a case in which the skin line image is projected onto the bottom portion 43 of the compression plate 40 and character information is projected onto the wall portion 44 (see FIG. 15), a surface (inner surface 44A) that intersects the surface (upper surface 43A) opposite to the contact surface 43B with the breast may be roughened in addition to the upper surface 43A as illustrated in a schematic diagram of FIG. 22. In addition, even in a case in which an outer surface 44B of the wall portion 44 is roughened, the display image is displayed on the wall portion 44. However, it is desirable that the outer surface 44B coming into contact with the chest wall is not roughened in order to suppress discomfort caused by the contact of the unevenness with the skin of the subject.

Further, for example, in a case in which both the bottom portion 43 and the wall portion 44 are small and it is difficult to project the projection image PP onto any surface as in the compression plate 40 for spot imaging, the projection image PP may be projected onto the support portion 46 that supports the compression plate 40. In this case, at least a partial region of at least one surface of the support portion 46 may be roughened.

In addition, in a case in which the region onto which the projection image PP can be projected is limited in each surface onto which the projection image PP is projected, only the region may be roughened.

It is preferable that the degree of roughening is equal to or smaller than the pixel size of the radiation detector 28 such that unevenness is not reflected in the radiographic image. In addition, as the roughness becomes smaller, the reflected light is more likely to diffuse. Therefore, it is possible to increase the visibility of the display image on the projection surface. On the other hand, in a case in which the roughness is too small, the breast is not seen through the compression plate. Therefore, it is preferable that the roughening is performed to the extent that the positioning of the breast is not hindered.

Specifically, in a case in which the projection surface of the compression plate 40 and the support portion 46 are configured to include the above-mentioned transparent resin, it is desirable that the arithmetic average roughness (Ra) of each roughened region is equal to or greater than 5 μm and equal to or less than 20 μm. In a case in which the arithmetic average roughness is equal to or less than 20 μm, it is possible to suppress the unevenness from being reflected in the radiographic image and to make it easy to see the display image on the projection surface. In a case in which the arithmetic average roughness is equal to or greater than 5 μm, it is suitable for checking the positioning of the breast through the compression plate 40. In other words, in a case in which the arithmetic average roughness is greater than 20 μm, the unevenness may be reflected in the radiographic image, which makes it difficult to see the display image on the projection surface. In a case in which the arithmetic average roughness is less than 5 µm, it may be difficult to see the breast through the compression plate 40.

As described above, the compression plate 40 according to this embodiment is a compression member that compresses the breast placed between the radiation source and the radiation detector. In the compression plate 40, at least a partial region of at least one surface that does not come into contact with the breast is roughened. Therefore, while the breast can be visually recognized through the compression plate 40, the display image can be displayed in a case in which the projection image PP is projected.

In addition, the use of the compression plate 40 and the support portion 46 whose projection surfaces are roughened such that light can be projected are not limited only to the mammography apparatus 10 according to the first and second embodiments of the present disclosure. The compression plate 40 and the support portion 46 can be used in any mammography apparatus including a radiation source, a radiation detector, a compression member which compresses the breast placed between the radiation source and the radiation detector and in which at least a partial region of at least one surface that does not come into contact with the breast is roughened, and an image projection unit that projects an image onto the roughened region of the compression member.

Further, as the compression plate 40 and the support portion 46 that can project light used in each of the above-described embodiments, the following configurations may be used in addition to the components subjected to the above-mentioned roughening process. For example, a transparent screen (see, for example, JP6606604B) that diffuses and/or reflects light projected by the projector 39 such that a display image can be visibly recognized and transmits light from the front and back surfaces may be attached to the projection surfaces of the compression plate 40 and the support portion 46. In this case, the transparent screen may be attached to the surfaces that come into contact with the skin of the subject, such as the contact surface 43B of the bottom portion 43 and the outer surface 44B of the wall portion 44. That is, the entire surfaces of the compression plate 40 and the support portion 46 can be used as the projection surfaces.

Further, in each of the above-described embodiments, the aspect in which the projection surface onto which the projection image PP (the guide information GI and the imaging information RI) is projected by the projector 39 is at least one surface of the compression plate 40 has been described. However, the present disclosure is not limited thereto. For example, the projector 39 may project the projection image PP onto the imaging table 30 of the mammography apparatus 10.

Further, in each of the above-described embodiments, the unit and method for generating the guide information GI are not particularly limited. For example, the guide information GI may be generated by the console 12, the mammography apparatus 10, or an external device on the basis of the radiographic image of the breast captured in the past. For example, the guide information GI may be a skin line image generated by dividing a radiographic image into a breast region and a blank region on the basis of the density of each pixel of the radiographic image and connecting the pixels which are the boundary points between the breast region and the blank region (see JP2010-051456A). Further, for example, the guide information GI related to one of the right breast and the left breast may be generated on the basis of a radiographic image of the other breast. Specifically, for example, in a case in which the radiographic image of the left breast is captured after the radiographic image of the right breast is captured, the guide information GI related to the left breast may be generated on the basis of an image obtained by reversing the radiographic image of the right breast in the left-right direction.

Furthermore, in each of the above-described embodiments, the guide information GI is used as the first information according to the present disclosure, and the imaging information RI including information indicating compression pressure is used as the second information according to the present disclosure. However, the first information and the second information are not limited thereto. For example, each of the first information and the second information may include plural information items. Moreover, the imaging information RI having different contents may be applied as the first information and the second information. For example, the imaging information RI including subject information may be used as the first information, and the imaging information RI including the information indicating the compression pressure may be used as the second information.

Further, in each of the above-described embodiments, the example in which the identification information is provided in the compression plate 40, the mammography apparatus 10 reads the identification information, and the acquisition unit 60 acquires the projection surface size information with reference to the identification information and the compression plate information 53 has been described. However, the present disclosure is not limited thereto. For example, the shape of the attached compression plate 40, such as the size of the bottom portion 43 and the height of the wall portion 44, may be measured to directly acquire the projection surface size information of the compression plate 40. For example, a device that measures the distance to an object to be imaged, such as a time-of-flight (TOF) camera, can be used as a unit for measuring the shape of the compression plate 40. Specifically, the TOF camera is a camera that captures a distance image using a TOF method, irradiates an object to be imaged with light, such as infrared rays, and measures the distance between the TOF camera and the object to be imaged on the basis of the time until reflected light is received or a phase change between the emitted light and the received light. In the distance image captured by the TOF camera, each pixel has distance information indicating the distance between the TOF camera and the object to be imaged. In a case in which the shape of the compression plate 40 as an object to be imaged changes, the distance information of each pixel also changes. Therefore, the type of the compression plate can be identified by capturing the image of the compression plate 40 with the TOF camera.

Further, in each of the above-described embodiments, the aspect in which the console 12 is an example of the information processing device according to the present disclosure has been described. However, devices other than the console 12 may have the functions of the information processing device according to the present disclosure. In other words, for example, the mammography apparatus 10 or an external device other than the console 12 may have some or all of the functions of the acquisition unit 60, the determination unit 62, the receiving unit 64, and the projection control unit 66.

In addition, in each of the above-described embodiments, the aspect in which the radiographic image and the compression plate information 53 are stored in the storage unit 52 of the console 12 has been described. However, the place in which the radiographic image and the compression plate information 53 are stored is not limited to the storage unit 52. For example, the radiographic image and the compression plate information 53 may be stored in the storage unit 22 of the mammography apparatus 10 or may be stored in a device outside the radiography system 1.

Further, in each of the above-described embodiments, for example, the following various processors can be used as the hardware structure of processing units performing various processes such as the acquisition unit 60, the determination unit 62, the receiving unit 64, and the projection control unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of plural FPGAs or a combination of a CPU and an FPGA). Further, plural processing units may be configured by one processor.

A first example of the configuration in which plural processing units are configured by one processor is an aspect in which one processor is configured by a combination of one or more CPUs and software and functions as plural processing units. A representative example of this aspect is a client computer or a server computer. A second example of the configuration is an aspect in which a processor that implements the functions of the entire system including plural processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the information processing program 51 is stored (installed) in the storage unit 52 in advance has been described. However, the present disclosure is not limited thereto. The information processing program 51 may be recorded on a recording medium, such as a compact disc read only memory (CD-ROM), a digital versatile disc read only memory (DVD-ROM), or a universal serial bus (USB) memory, and then provided. In addition, the information processing program 51 may be downloaded from an external device through the network. Furthermore, the technology of the present disclosure extends to a storage medium that non-temporarily stores the information processing program, in addition to the information processing program.

In the technology of the present disclosure, the above-described embodiments may be appropriately combined with each other. The contents described and illustrated above are detailed descriptions of portions related to the technology of the present disclosure and are merely examples of the technology of the present disclosure. For example, the description of the configurations, functions, operations, and effects is the description of examples of the configurations, functions, operations, and effects of portions related to the technology of the present disclosure. Therefore, unnecessary portions may be deleted or new elements may be added or replaced in the contents described and illustrated above, without departing from the scope and spirit of the technology of the present disclosure.

All of the documents, the patent applications, and the technical standards described in the specification are incorporated by reference herein to the same extent as each individual document, each patent application, and each technical standard are specifically and individually stated to be incorporated by reference.

What is claimed is:

1. An information processing device comprising at least one processor, wherein the processor is configured to control an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

2. The information processing device according to claim 1, wherein the processor is configured to:
receive a selection instruction to select the first information and the second information projected onto the first projection surface; and
switch the first information and the second information projected onto the first projection surface on the basis of the selection instruction.

3. The information processing device according to claim 1, wherein the processor is configured to switch the first information and the second information projected onto the first projection surface for a period for which the breast is positioned between the radiation source and the radiation detector and a period after the positioning is completed.

4. The information processing device according to claim 1, wherein the processor is configured to switch the first information and the second information projected onto the first projection surface according to a compression pressure of the breast by the compression member.

5. The information processing device according to claim 1, wherein the processor is configured to switch the first information and the second information projected onto the first projection surface according to a thickness of the breast in a compression direction in which the breast is compressed.

6. The information processing device according to claim 1, wherein the processor is configured to:
acquire projection surface size information indicating a size of the first projection surface; and
change a relative position of the first information and the second information projected onto the first projection surface depending on the size of the first projection surface indicated by the projection surface size information.

7. The information processing device according to claim 1, wherein the processor is configured to:
acquire projection surface size information indicating a size of the first projection surface;
perform control to project both the first information and the second information onto the first projection surface in a case in which the projection surface size information indicates that the first projection surface is equal to or larger than a predetermined size; and
perform control to project either the first information or the second information onto the first projection surface in a case in which the projection surface size information indicates that the first projection surface is smaller than the predetermined size.

8. The information processing device according to claim 1, wherein:
the image projection unit projects an image onto a second projection surface different from the first projection surface of the compression member in addition to the first projection surface, and
the processor is configured to control the image projection unit such that the first information and the second information are projected onto different projection surfaces of the first and second projection surfaces.

9. The information processing device according to claim 1, wherein the processor is configured to perform control to project the first information and the second information in different display aspects.

10. The information processing device according to claim 1, wherein:
the first information is guide information that serves as a guide in a case in which the breast is positioned, and
the second information is imaging information including at least one of information indicating a compression pressure of the breast by the compression member, information indicating a thickness of the breast in a compression direction in which the breast is compressed, subject information indicating a subject pertaining to the breast as an object to be imaged, radiographer information indicating a radiographer who performs imaging, date information indicating a date of imaging, or angle information indicating an angle at which an image of the breast is captured.

11. An information processing method comprising:
controlling an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

12. A non-transitory computer-readable storage medium storing an information processing program that causes a computer to perform a process of:
controlling an image projection unit which projects a projection image onto a first projection surface of a compression member disposed between a radiation source and a radiation detector in a mammography apparatus that irradiates a breast compressed by the compression member with radiation to capture a radiographic image such that at least one of first information or second information is switchably projected onto the first projection surface.

* * * * *